United States Patent
Unser

(10) Patent No.: US 11,170,890 B2
(45) Date of Patent: Nov. 9, 2021

(54) DEVICES SYSTEMS AND METHODS FOR EVALUATING BLOOD FLOW WITH VASCULAR PERFUSION IMAGING

(71) Applicant: KONINKLIJKE PHILIPS N.V., Eindhoven (NL)

(72) Inventor: John Unser, Temecula, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/153,746

(22) Filed: Oct. 6, 2018

(65) Prior Publication Data

US 2019/0108906 A1 Apr. 11, 2019

Related U.S. Application Data

(60) Provisional application No. 62/569,030, filed on Oct. 6, 2017.

(51) Int. Cl.
*G16H 30/40* (2018.01)
*A61B 6/03* (2006.01)
(Continued)

(52) U.S. Cl.
CPC ........... *G16H 30/40* (2018.01); *A61B 5/0275* (2013.01); *A61B 6/032* (2013.01); *A61B 6/463* (2013.01);
(Continued)

(58) Field of Classification Search
CPC ... G06T 11/206; G06T 11/60; G06T 2200/24; G06T 2207/20104; G06T 2207/30104;
(Continued)

(56) References Cited

U.S. PATENT DOCUMENTS

| 2004/0006266 A1* | 1/2004 | Ustuner | A61B 8/08 600/407 |
| 2006/0098010 A1* | 5/2006 | Dwyer | G06T 19/006 345/424 |

(Continued)

FOREIGN PATENT DOCUMENTS

JP 05433282 B2 3/2014

OTHER PUBLICATIONS

International Search Report and Written Opinion, International application No. PCT/EP2018/077124, dated Jan. 23, 2019.

*Primary Examiner* — Jennifer Mehmood
*Assistant Examiner* — Kim Thanh T Tran

(57) ABSTRACT

Devices, systems, and methods for evaluating blood flow with vascular perfusion imaging are disclosed. In an embodiment, a medical system is disclosed. One embodiment of the medical system comprises a perfusion imaging system configured to obtain perfusion imaging data associated with movement of contrast through a vessel of a patient, a graphical user interface, and a medical processing unit in communication with the perfusion imaging system and the graphical user interface. The medical processing unit is configured to receive a first set of perfusion imaging data from the perfusion imaging system, determine at least one parameter representative of the movement of the contrast through the vessel of the patient, generate a first graphical representation of the first set of perfusion imaging data and the at least one parameter determined based on the first set of perfusion imaging data, and output the first graphical representation to the graphical user interface.

17 Claims, 6 Drawing Sheets

(51) Int. Cl.
*A61B 6/00* (2006.01)
*G16H 50/50* (2018.01)
*G16H 50/20* (2018.01)
*A61B 5/0275* (2006.01)
*G06T 7/00* (2017.01)
*G06T 7/20* (2017.01)
*G06T 11/20* (2006.01)
*G06T 11/60* (2006.01)
*A61B 5/00* (2006.01)

(52) U.S. Cl.
CPC ............ *A61B 6/507* (2013.01); *G06T 7/0016* (2013.01); *G06T 7/20* (2013.01); *G06T 11/206* (2013.01); *G06T 11/60* (2013.01); *G16H 50/20* (2018.01); *G16H 50/50* (2018.01); *A61B 5/743* (2013.01); *A61B 6/486* (2013.01); *A61B 6/5217* (2013.01); *G06T 2200/24* (2013.01); *G06T 2207/20104* (2013.01); *G06T 2207/30104* (2013.01)

(58) Field of Classification Search
CPC ......... G06T 7/0016; G06T 7/20; G16H 30/40; G16H 50/20; G16H 50/50; A61B 6/463; A61B 6/507; A61B 6/032; A61B 5/0275; A61B 6/486; A61B 6/5217; A61B 5/743

USPC ....................................................... 345/629
See application file for complete search history.

(56) References Cited

U.S. PATENT DOCUMENTS

| | | | |
|---|---|---|---|
| 2007/0016016 A1* | 1/2007 | Haras | G06K 9/3233 600/431 |
| 2010/0259550 A1* | 10/2010 | Baumgart | A61B 6/463 345/589 |
| 2011/0015520 A1* | 1/2011 | Meetz | A61B 6/507 600/425 |
| 2013/0208957 A1* | 8/2013 | Wiesner | A61B 5/0033 382/128 |
| 2013/0218028 A1* | 8/2013 | Mestha | A61B 5/02125 600/479 |
| 2015/0071520 A1 | 3/2015 | Takemoto et al. | |
| 2015/0161800 A1 | 6/2015 | Nagae et al. | |
| 2015/0320325 A1* | 11/2015 | Sheehan | A61B 6/5247 600/423 |
| 2016/0203603 A1* | 7/2016 | Li | G01R 33/56366 382/131 |
| 2016/0287099 A1* | 10/2016 | Kobayashi | A61B 5/02422 |
| 2017/0140532 A1* | 5/2017 | Dascal | A61B 6/5247 |
| 2017/0178319 A1* | 6/2017 | Sugiura | G01R 33/5602 |
| 2018/0085170 A1* | 3/2018 | Gopinath | G16H 50/30 |

\* cited by examiner

DEVICES SYSTEMS AND METHODS FOR EVALUATING BLOOD FLOW WITH VASCULAR PERFUSION IMAGING

TECHNICAL FIELD

The present disclosure relates generally to the assessment and treatment of disease within the circulatory system. Aspects of the present disclosure include using perfusion assessment to determine the completeness of an intravascular therapy.

BACKGROUND

Diseases of the circulatory system can be life-threatening and affect millions of people worldwide. One common problem is the accumulation of plaque inside a blood vessel. Over time, a buildup of plaque may occlude the blood vessel. Occlusion of blood vessels increases the likelihood of a blockage, thereby putting the afflicted individual at an elevated risk of heart attack or stroke. Occlusion also reduces blood flow. Reduced blood flow can result in a number of deleterious conditions. For example, in some cases, occluded vessels may reduce blood flow to the limbs and thereby give rise to peripheral artery disease (PAD). PAD occurs when the extremities, most commonly the legs, fail to receive sufficient blood flow resulting in symptoms which may include one or more of cramping, pain, numbness, weakness, color change, and weak pulse. Depending on the severity of an individual's condition, medical intervention may be advisable.

Accordingly, there remains a need for improved devices, systems, and methods for assessing and treating circulatory diseases. In that regard, the devices, systems, and associated methods of the present disclosure overcome one or more shortcomings of the prior art.

SUMMARY

The present application relates to improving a physician's ability evaluate blood flow through a vessel of a patient. A medical imaging device known as a perfusion imaging tracks the movement of a contrast medium that is introduced into the blood stream and moves, along with the blood, through the vessel. The computer system in communication with the perfusion imaging device determines one or more parameters associated with the movement of the contrast medium that provide helpful information to the physician to assess the health of the vessel. The computer system can present the information representative of the movement of contrast through the vessel, such as with a graph or numerical values, to a display so that the physician can efficiently evaluate blood flow. In some instances, the assessment is performed before and after an intravascular therapy (such as positioning a stent within the vessel). The graphical display can include pre-procedure and post-procedure information for the physician to readily compare the parameters. Accordingly, the physician can easily assess the efficacy of the treatment.

In one embodiment, a medical system is disclosed. The medical system comprises a perfusion imaging system configured to obtain perfusion imaging data associated with movement of contrast through a vessel of a patient, a graphical user interface, and a medical processing unit in communication with the perfusion imaging system and the graphical user interface. The medical processing unit is configured to receive a first set of perfusion imaging data from the perfusion imaging system, determine, based on the first set of perfusion imaging data, at least one parameter representative of the movement of the contrast through the vessel of the patient, generate a first graphical representation of the first set of perfusion imaging data and the at least one parameter determined based on the first set of perfusion imaging data, and output the first graphical representation to the graphical user interface for display.

In some embodiments, the medical processing unit is further configured to receive a user selection of a region of interest. In some embodiments, the at least one parameter comprises at least one of arrival time, time to peak, wash in rate, width, area under curve, or mean transit time. In some embodiments, the first graphical representation comprises a graph representative of the movement of contrast through the vessel of the patient. In some embodiments, the medical processing unit is further configured to receive a second set of perfusion imaging data from the perfusion imaging system, determine, based on the second set of perfusion imaging data, at least one parameter representative of the movement of the contrast through the vessel of the patient, generate a second graphical representation of the second set of perfusion imaging data and the at least one parameter determined based on the second set of perfusion imaging data, and output the second graphical representation to the graphical user interface for display. In some embodiments, the first set of perfusion imaging data comprises perfusion imaging data obtained prior to an intravascular procedure and the second set of perfusion imaging data comprises perfusion imaging data obtained after the intravascular procedure. In some embodiments, outputting the first graphical representation and the second graphical representation to the graphical user interface for display comprises combining the first graphical representation and the second graphical representation to form a third graphical representation comprising a first curve representative of the movement of the contrast through the vessel of the patient as shown in the first graphical representation and a second curve representative of the movement of the contrast through the vessel of the patient as shown in the second graphical representation both plotted on the same set of axes. In some embodiments, the medical processing unit is configured to generate a recommendation based on the at least one parameter determined based on the first set of perfusion imaging data and to output the recommendation to the graphical user interface for display. In some embodiments, the recommendation comprises identifying one or more candidate sites for an intravascular procedure.

In one embodiment, a method is disclosed. The method comprises receiving, by a medical processing unit, a first set of perfusion imaging data from a perfusion imaging system configured to obtain perfusion imaging data associated with movement of contrast through a vessel of a patient, determining, by the medical processing unit, based on the first set of perfusion imaging data, at least one parameter representative of the movement of the contrast through the vessel of the patient, generating, by the medical processing unit, a first graphical representation of the first set of perfusion imaging data and the at least one parameter determined based on the first set of perfusion imaging data, and outputting, from the medical processing unit, the first graphical representation to a graphical user interface for display.

In some embodiments, the at least one parameter comprises at least one or arrival time, time to peak, wash in rate, width, area under curve, or mean transit time. In some embodiments, the first graphical representation comprises a graph representative of the movement of contrast through the vessel of the patient. In some embodiments, the method further comprises generating, by the medical processing unit, a first perfusion image of an anatomical structure based on the first set of perfusion imaging data, and outputting, from the medical processing unit, the first perfusion image to the graphical user interface for display. In some embodiments, the method further comprises generating, by the medical processing unit, a recommendation based on the first set of perfusion imaging data, wherein generating the recommendation comprises identifying one or more candidate sites for an intravascular procedure, and outputting, from the medical processing unit, the recommendation to the graphical user interface for display. In some embodiments, identifying one or more candidate sites for the intravascular procedure comprises providing a visual indicator of the one or more candidate sites on the anatomical structure shown in the first perfusion image.

In one embodiment, a method is disclosed. The method comprises receiving, by the medical processing unit, a second set of perfusion imaging data from the perfusion imaging system, determining, by the medical processing unit, based on the second set of perfusion imaging data, at least one parameter representative of the movement of the contrast through the vessel of the patient, generating, by the medical processing unit, a second graphical representation of the second set of perfusion imaging data and the at least one parameter determined based on the second set of perfusion imaging data, and outputting, from the medical processing unit, the second graphical representation to the graphical user interface for display.

In some embodiments, the method further comprises determining, by the medical processing unit, the difference between the at least one parameter determined based on the second set of perfusion imaging data and the at least one parameter determined based on the first set of perfusion imaging data, and outputting, from the medical processing unit, the difference to the graphical user interface for display. In some embodiments, the first set of perfusion imaging data comprises perfusion imaging data obtained prior to an intravascular procedure and the second set of perfusion imaging data comprises perfusion imaging data obtained after the intravascular procedure. In some embodiments, the method further comprises generating, by the medical processing unit, a second perfusion image of the anatomical structure based on the second set of perfusion imaging data, and outputting, from the medical processing unit, the second perfusion image to the graphical user interface for display. In some embodiments, outputting the first graphical representation and the second graphical representation to the graphical user interface for display comprises combining the first graphical representation and the second graphical representation to form a third graphical representation comprising a first curve representative of the movement of the contrast through the vessel of the patient as shown in the first graphical representation and a second curve representative of the movement of the contrast through the vessel of the patient as shown in the second graphical representation both plotted on the same set of axes.

Additional aspects, features, and advantages of the present disclosure will become apparent from the following detailed description

BRIEF DESCRIPTIONS OF THE DRAWINGS

Illustrative embodiments of the present disclosure will be described with reference to the accompanying drawings, of which:

DETAILED DESCRIPTION

Figure 1:
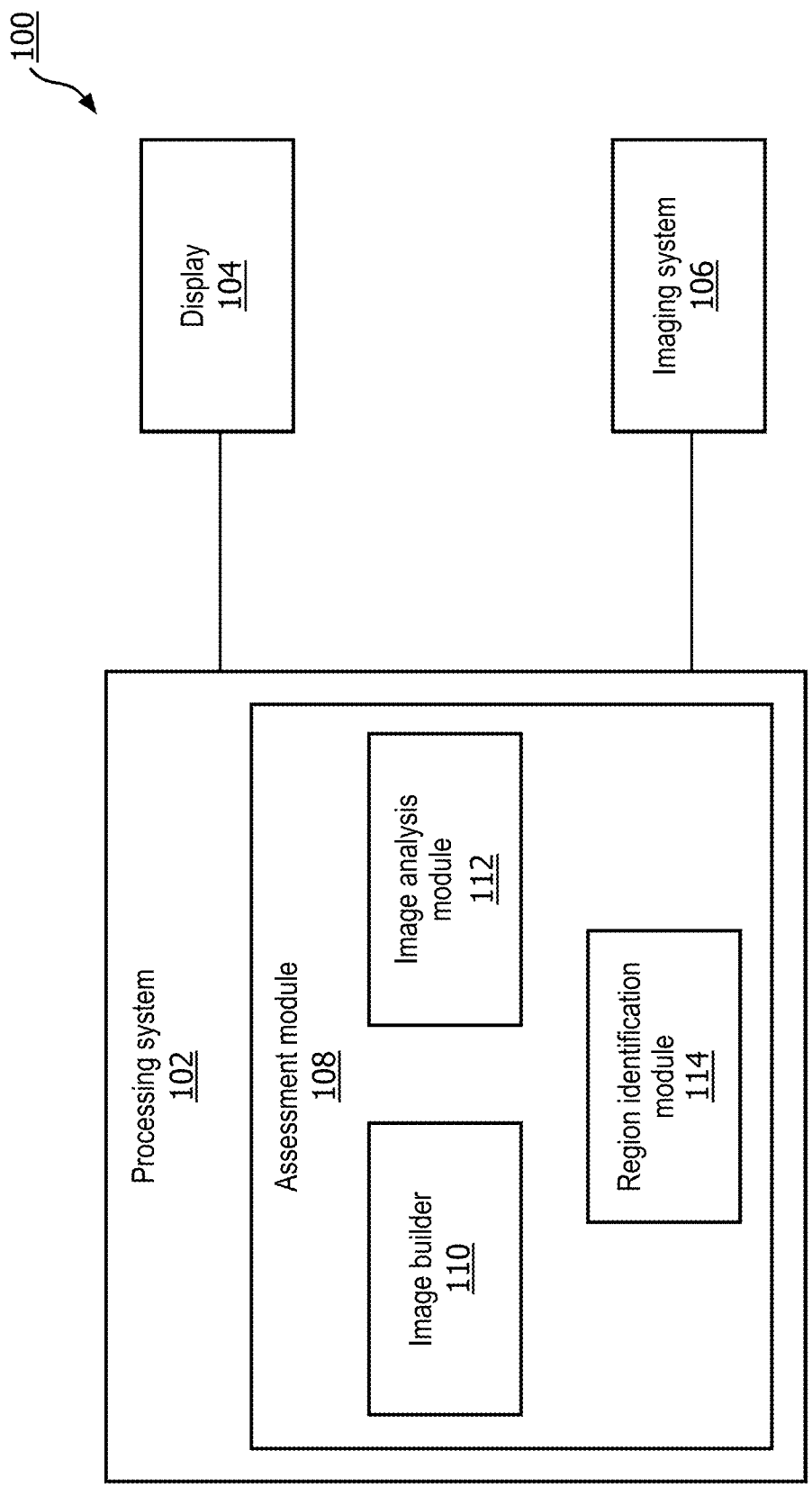
FIG. 1 is a schematic illustration of a system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. It is emphasized that, in accordance with the standard practice in the industry, some of the illustrated features may not be drawn to scale. In fact, the dimensions of various features may be arbitrarily increased or reduced for clarity. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Turning now to FIG. 1, a system 100 is described. The system 100 comprises a medical processing system 102, a display 104, and a perfusion imaging system 106. In some circumstances, the system 100 may comprise one or more additional elements. The medical processing system 102 comprises a perfusion assessment module 108. The perfusion assessment module 108 comprises an image builder 110, an image analysis module 112, and a region identification module 114. The perfusion assessment module 108, image builder 110, image analysis module 112, and region identification module 114 may be implemented in hardware, implemented in software, or implemented in some combination of hardware and software.

The system 100 may be deployed in a hospital, e.g., in a catheterization laboratory or imaging suite. The medical processing system 102 may be located in a control room associated with the catheterization laboratory or imaging suite. Optionally, the medical processing system 102 may be located elsewhere, such as in the catheterization laboratory or imaging suite itself. The catheterization laboratory and/or imaging suite and control room may be used to perform any number of medical sensing procedures such as angiography, e.g., digital subtraction angiography (DSA) or perfusion angiography, fluoroscopy, IVUS, virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, other medical sensing modalities, or combinations thereof.

The display 104 and/or the perfusion imaging system 106 may be directly or indirectly communicatively coupled to the medical processing system 102. These elements may be communicatively coupled to the medical processing system 102 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The medical processing system 102 may be communicatively coupled to one or more data networks, e.g., a TCP/IP-based local area network (LAN). In other embodiments, different protocols may be utilized such as Synchronous Optical Networking (SONET). In some cases, the medical processing system 102 may be communicatively coupled to a wide area network (WAN). The medical processing system 102 may utilize network connectivity to access various resources. For example, the medical processing system 102 may communicate with a Digital Imaging and Communications in Medicine (DICOM) system, a Picture Archiving and Communication System (PACS), and/or a Hospital Information System via a network connection.

In some cases, the system 100 may be used to assess a subject's, e.g., a patient's, circulation. In particular, the system 100 may be used to assess the circulation in a subject's brain, kidneys, limbs, e.g., legs, extremities, e.g., hands and feet, or combinations thereof. In that regard, the perfusion imaging system 106 may be used to obtain perfusion imaging data about an area of the subject's body. The perfusion imaging data may comprise data about blood flow through the subject's vasculature, e.g., data about blood flow through an imaged area. Accordingly, the perfusion imaging system 106 may comprise one or more imaging systems configured to obtain data about blood flow through the subject's vasculature. For example, the perfusion imaging system 106 may comprise an angio system configured to perform angiography, e.g., DSA. In some cases, obtaining data about blood flow through the subject's vasculature may comprise injecting the subject with a solution configured to enhance resolution of the subject's blood. For example, the subject may be injected with one or more of a radioisotope or contrast media. Thus, in some cases, the perfusion imaging system 106 may be configured to obtain perfusion imaging data associated with the movement of contrast through the vasculature and/or individual vessels of the subject. Indeed, movement of contrast may be treated as a proxy for movement of blood. Hence, reference herein to movement of contrast may be assumed to implicate movement of blood.

The perfusion imaging system 106 may communicate the perfusion imaging data to the medical processing system 102. The medical processing system 102 may receive the perfusion imaging data and route the received perfusion imaging data to the perfusion assessment module 108. The image builder 110 of the perfusion assessment module 108 may generate one or more images based on the perfusion imaging data received from the perfusion imaging system 106 and may output the one or more images to the display 104. The display 104 may comprise multiple screens, and different screens may be configured to display different images and/or the same images. In that regard, multiple images may be displayed on each screen. In some cases, the display 104 may be representative of a user interface (UI), e.g., a graphical user interface (GUI), that provides a user, e.g., a physician, feedback about a procedure. The images outputted from the image builder 110 to the display 104 may comprise perfusion images of an anatomical structure imaged by the perfusion imaging system 106, graphical representations of the perfusion imaging data, representations of one or more parameters calculated based on the perfusion imaging data, or combinations thereof. Graphical representations of the perfusion imaging data may comprise one or more graphs representative of the movement of contrast through a vessel of a subject. Perfusion images of anatomical structures may depict the subject's vasculature, the vessels of which may be color coded indicative of flow.

In some cases, the image builder 110 may receive multiple sets of perfusion imaging data from the perfusion imaging system 106. For example, one set of perfusion imaging data may be obtained prior to a therapy or treatment, e.g., an intravascular therapy such as balloon angioplasty, stent placement, recanalization, etc., and a second set of perfusion imaging data may be obtained after the therapy or treatment. Both sets of perfusion imaging data may be sent from the perfusion imaging system 106 to the image builder 110. The various sets of perfusion imaging data may be sent to the image builder 110 as they are obtained or in aggregate after all sets are obtained. The image builder 110 may output images generated based on the sets of perfusion imaging data as the sets are received or after all sets are received.

When the image builder 110 receives multiple sets of perfusion imaging data, the image builder 110 may generate and output to the display 104 one or more images for each set of perfusion imaging data. For example, the image builder 110 may receive a first set of perfusion imaging data obtained prior to an intravascular procedure to improve one or more aspects of a subject's circulation and a second set of perfusion imaging data obtained after the intravascular procedure and may generate and output to the display 104 a first perfusion image of an anatomical structure based on the first set of perfusion imaging data and a second perfusion image of the anatomical structure based on the second set of perfusion imaging data. The image builder 110 may additionally or alternatively generate and output to the display 104 a first graphical representation based on the first set of perfusion imaging data and a second graphical representation based on the second set of perfusion imaging data. In some cases, the image builder 110 may combine multiple graphical representations, e.g., the first and second graphical representations, to form a graphical representation, e.g., a third graphical representation, comprising multiple curves representative of the movement of contrast, blood, or both, through a vessel as shown in the various graphical representations such that the multiple curves are plotted on the same set of axes.

The image analysis module 112 of the perfusion assessment module 108 may analyze the perfusion imaging data, the images generated by the image builder 110, or both. For the sake of brevity, the description of some embodiments includes that the analysis of the image analysis module 112 may be based on images generated by the image builder 110 without specifying that the analysis may also be based on the perfusion imaging data or vice versa. In such cases, it should be understood that the analysis of the image analysis module 112 may be additionally or alternatively based on the unspecified perfusion imaging data or images generated by the image builder 110. The image analysis module 112 may analyze perfusion imaging data and generate graphical data about the movement of contrast, blood flow, or both through a vessel of a subject based on the perfusion imaging data and may communicate the graphical data to the image builder 110, which may generate a graphical representation of the perfusion imaging data based on the graphical data. The image analysis module 112 may determine at least one parameter representative of movement of contrast, movement of blood, or both, through a vessel based on the perfusion imaging data, the images generated by the image builder 110, or both. Parameters representative of movement of contrast, blood, or both, through a vessel include: arrival time, time to peak, wash in rate, width, area under curve, and mean transit time. The image analysis module 112 may communicate the at least one parameter to the image builder 110, which may then generate a representation of the at least one parameter, e.g., a numeric value, an alpha numeric label, etc., and output the representation of the at least one parameter to the display 104.

In some cases, the image analysis module 112 may analyze perfusion imaging data, images generated by the image builder 110, or both, and may generate a recommendation based on the perfusion imaging data, images generated by the image builder 110, the at least one parameter, or combinations thereof. The recommendation may comprise identifying one or more candidate sites for an intravascular procedure, identifying a specific procedure to be performed, recommending that a procedure be repeated, recommending that a planned procedure be canceled, recommending follow up action after a procedure has been performed, or combinations thereof. For example, the image analysis module 112 may analyze a perfusion image of an anatomical structure and may determine that, based on movement of contrast through a subject's vasculature, performance of an intravascular therapy at one or more sites within the subject's vasculature would improve blood flow to one or more areas of the anatomical structure and make a treatment site recommendation based on the determination. The image analysis module 112 may have access to one or more databases storing information about intravascular procedures, past procedures performed, follow up actions performed following unsuccessful initial procedures, treatment sites, improvement statistics indexed based on procedure and/or treatment site, or combinations thereof. Generating the recommendation may comprise comparing perfusion imaging data, images generated by the image builder 110, the at least one parameter, or combinations thereof to information stored in the one or more databases. The image analysis module 112 may communicate the recommendation to the image builder 110. The image builder 110 may incorporate the recommendation into one or more images generated based on the perfusion imaging data. For example, the image builder 110 may provide a visual indicator on a perfusion image of an anatomical structure that identifies a recommended site for performance of an intravascular therapy.

In some cases, a user of the system 100, e.g., a physician, may wish to evaluate a particular region of interest of a subject's anatomy, e.g., the ball of the subject's foot. In that regard, the user may provide the region of interest to the medical processing system 102. The user may indicate the region of interest by drawing free form on a perfusion image of an anatomical structure displayed on the display 104, which may comprise a capacitive touch screen, a resistive touch screen, or combinations thereof. The indicated region of interest may be communicated to the region identification module 114. The user may indicate the region of interest by selecting a shape from a list of shapes, adjusting the size of the shape, and placing the shape over the perfusion image of the anatomical structure to bound the region of interest. The user may select a region of interest from a drop down menu of possible regions of interest. For example, the user may indicate that the perfusion image of the anatomical structure comprises a perfusion image of a subject's foot whereupon the region identification module 114 may output a list of possible regions of interest, e.g., toes, ball of the foot, arch of the foot, heel, ankle, etc., from which the user may make a selection. In that regard, different lists including different regions of interest may be presented to the user for different anatomical structures. In some cases, the image analysis module 112 may automatically identify the anatomical structure in an image and may communicate the identity of the anatomical structure to the region identification module 114, which may automatically select the list of regions of interest that corresponds to the anatomical structure. The region identification module 114 may update the list of possible regions of interest as new regions of interest are identified by the user.

The region identification module 114 may communicate the indicated region of interest to the image analysis module 112, the image builder 110, or both. For example, the region identification module 114 may communicate the indicated region of interest to the image analysis module 112 which may determine for the region of interest at least one parameter representative of movement of contrast, movement of blood, or both, through a vessel based on perfusion imaging data pertaining to the region of interest. The image analysis module 112 may then communicate the at least one parameter determined for the region of interest to the image builder 110 for output to the display 104. The image builder 110 may indicate the region of interest on images outputted to the display 104. In some cases, a user may wish to adjust the region of interest. In such cases, upon receiving the adjusted region of interest from the region identification module 114, the image analysis module 112 may automatically update the determination of the at least one parameter to reflect adjusted region of interest.

Figure 2A:
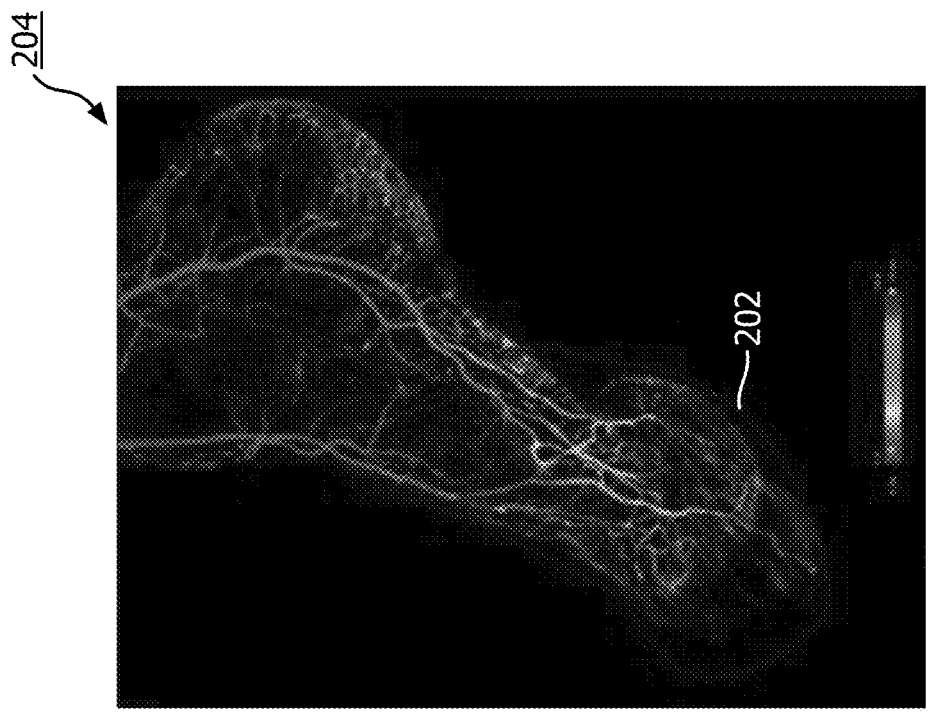
FIG. 2A is a visual display according to an embodiment of the present disclosure.

Turning now to FIG. 2A, shown therein is a visual display of an image 200. The image 200 may have been generated by the image builder 110 as described herein and may be displayed on the display 104. The image 200 comprises a pre-treatment perfusion image of an anatomical structure. The anatomical structure shown in FIG. 2A is a subject's foot. The image 200 comprises an indicated region of interest 202, in particular a region of interest that has been drawn free form by a user. The image 200 further comprises a depiction of the subject's vasculature, the vessels of which may be color coded indicative of flow. Moving toward the red end of the color spectrum may indicate increases in flow, where red is indicative of good or unobstructed flow, while moving toward the blue end of the color spectrum may indicate decreases in flow, where blue is indicative of poor or obstructed flow. The significance of the colors may be reversed in some implementations. As can be seen in FIG. 2A, there is little blood flow near the periphery of the region of interest 202.

Figure 2B:
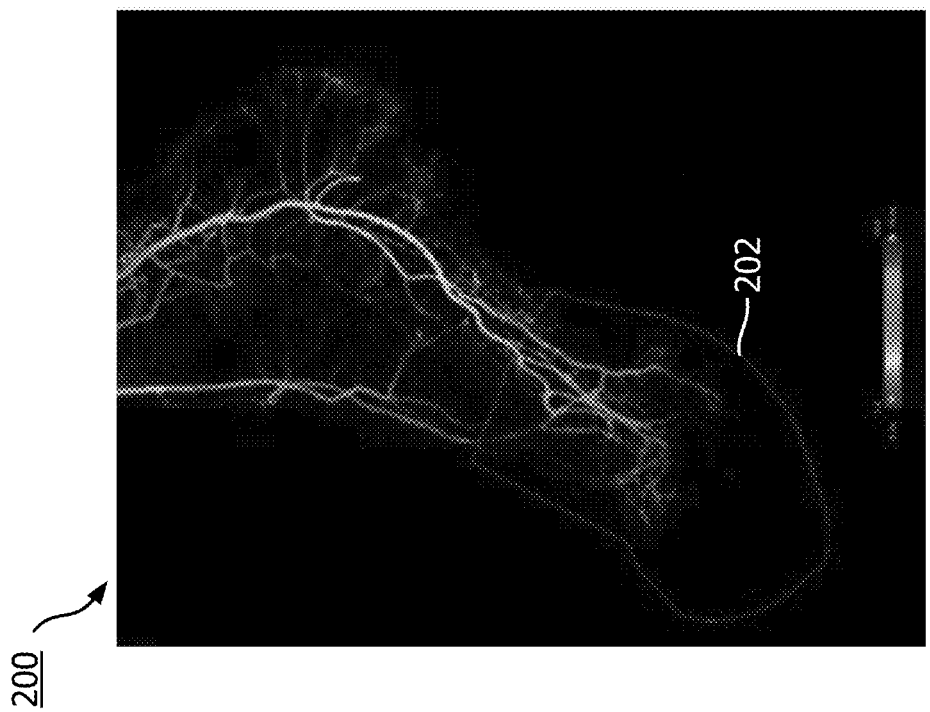
FIG. 2B is a visual display according to another embodiment of the present disclosure.

Turning now to FIG. 2B, shown therein is a visual display of an image 204. The image 204 may have been generated by the image builder 110 as described herein and may be displayed on the display 104. In that regard, the image 204 may be displayed alongside the image 200 either on the same screen or on a different screen. The image 204 comprises a post-treatment perfusion image of the anatomical structure shown in FIG. 2A, the subject's foot. The image 204 retains the indicated region of interest 202. Alternatively or additionally, an image representing the difference between pre- and post-treatment perfusion may be derived from images 204 and 200, retaining the indicated region of interest 202, accentuating the effect of the treatment on the perfusion. As can be seen in FIG. 2B, blood flow near the periphery of the region of interest 202 has increased along with blood flow in other areas of the subject's foot. Such increases may be indicative that an intravascular procedure undertaken to improve the subject's circulation was successful. Unfortunately, in some cases, perfusion imaging of an anatomical structure alone may be insufficient to assess the success of treatment. Unsuccessful treatment can result in prolonged circulatory problems and may result in amputation in some cases. Accordingly, in order to improve the accuracy of treatment assessment, it may be beneficial to perform additional analyses on perfusion imaging data obtained by the perfusion imaging system 106, e.g., by determining at least one parameter representative of movement of contrast, movement of blood, or both, through a vessel based on the perfusion imaging data.

Figure 3:
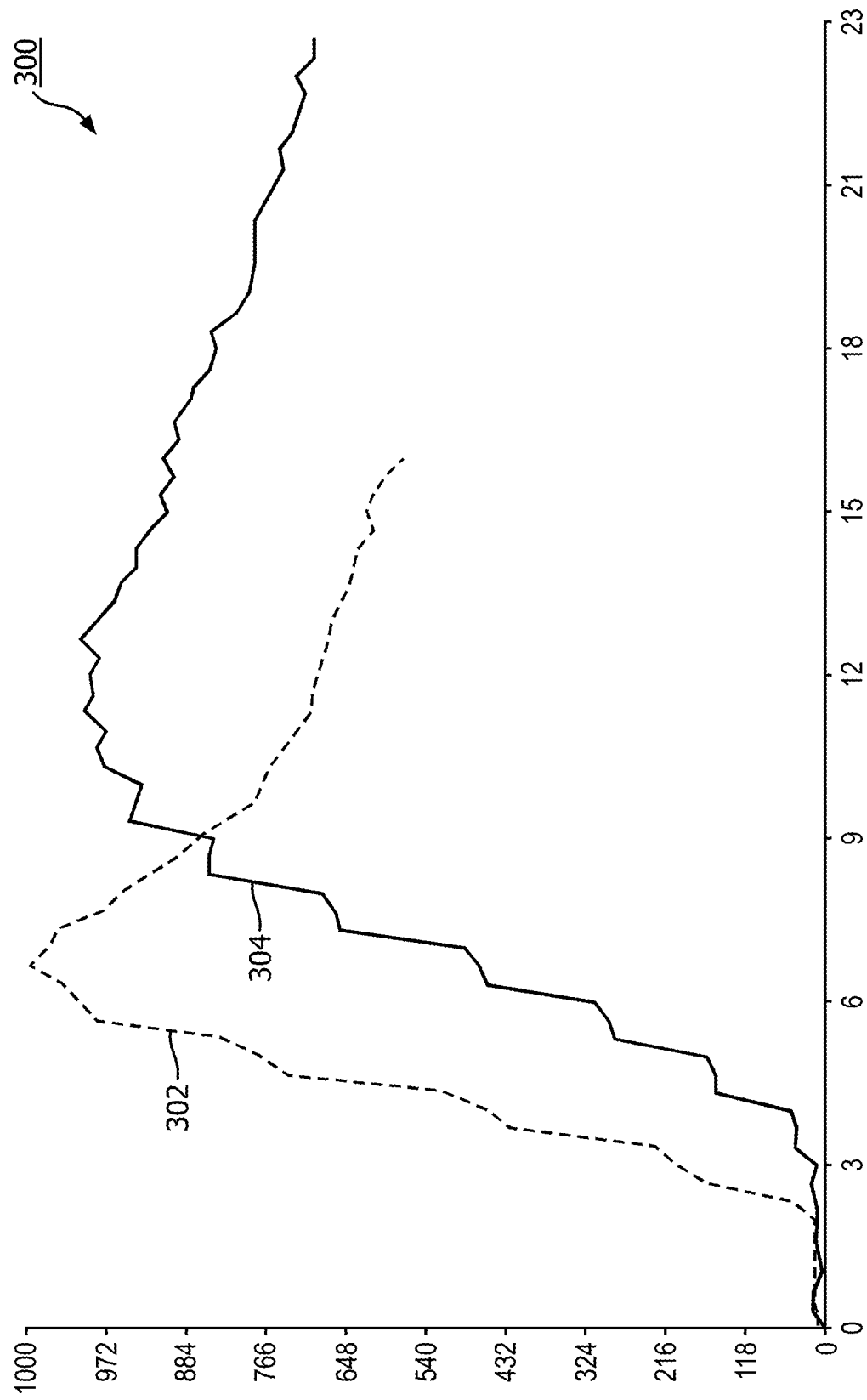
FIG. 3 is a visual display according to another embodiment of the present disclosure.

Turning now to FIG. 3, shown therein is a visual display of an image 300. The image 300 may have been generated by the image builder 110 as described herein and may be displayed on the display 104. In some instances, the image 300 may be generated based on pre and post-treatment perfusion imaging data for the region of interest 202. In that regard, the image 300 may be displayed along with one or both of the images 200 and 204 either on the same screen or on different screens. The image 300 comprises a graphical representation of two sets of perfusion imaging data, one set obtained prior to performance of an intravascular procedure and the other set obtained after performance of the intravascular procedure. In that regard, the image 300 comprises curve 304 representative of movement of contrast through a vessel of a subject prior to performance of the intravascular procedure and curve 302 representative of movement of contrast through the vessel of the subject after performance of the intravascular procedure. As shown, curve 304 and curve 302 may be plotted on the same set of axes. In FIG. 3, the 'X' axis is representative of time in seconds and the "Y" axis is representative of density in Hounsfield units (HU). In some cases, the 'Y' axis may be representative density in grams per cubic centimeter. As described in greater detail below, the curve 304 and the curve 302 may be analyzed to determine one or more parameters representative of movement of contrast, movement of blood, or both, through the vessel, which may improve assessment of the success of the intravascular procedure.

Figure 4:
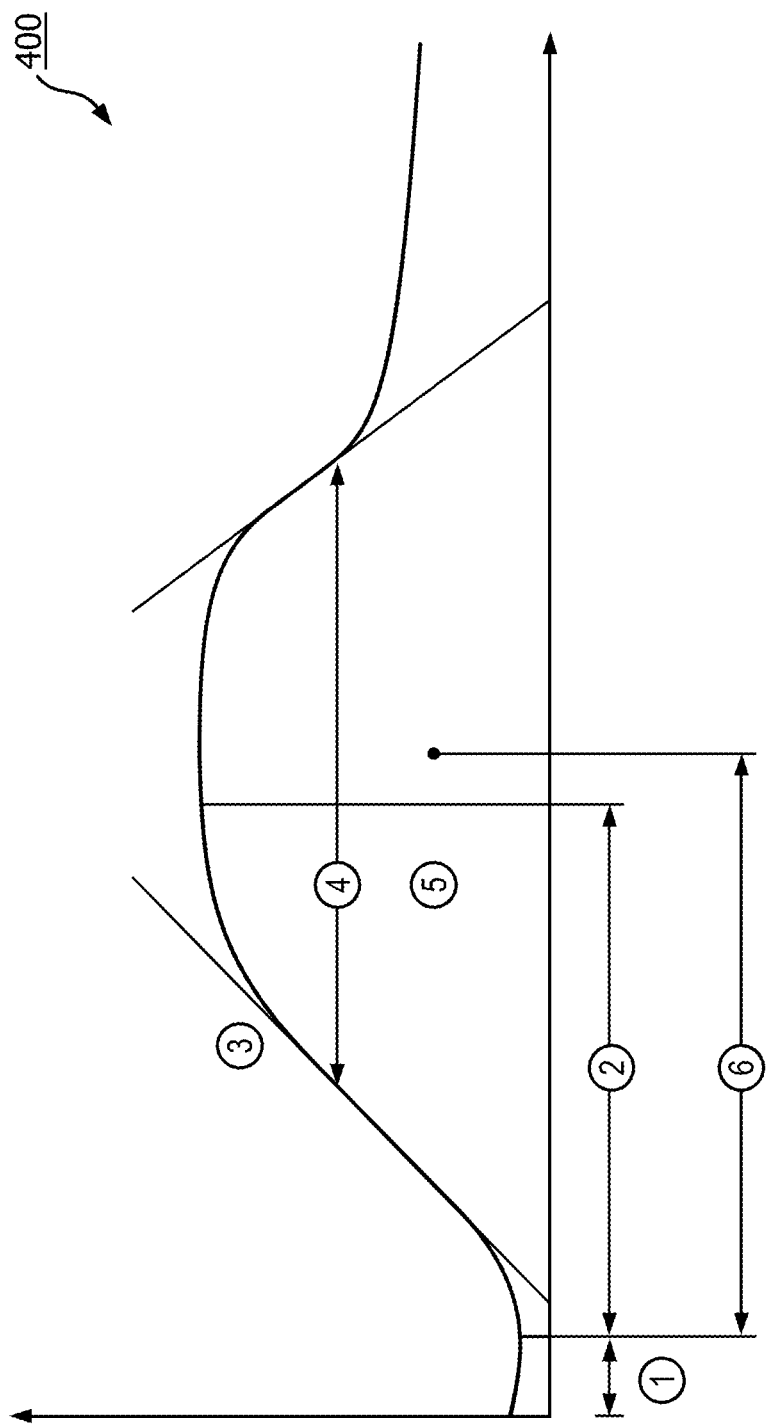
FIG. 4 is a visual display according to another embodiment of the present disclosure.

Turning now to FIG. 4, shown therein is a visual display of an image 400. The image 400 may have been generated by the image builder as described herein and may be displayed on the display 104. In that regard, the image 400 may be displayed along with the image 200, the image 204, the image 300, or combinations thereof, on the same screen or on different screens. In some cases, the image 400 may be used as a legend serving to indicate how the value of each parameter representative of movement of contrast, movement of blood, or both, through a vessel is determined. In that regard, labels indicating how the value of each parameter is determined may be applied to graphical representations generated based on perfusion imaging data.

The image 400 comprises labels 1-6 indicating how six parameters representative of movement of contrast, movement of blood, or both, through a vessel are determined. Label 1 indicates arrival time. Arrival time is the time between the start of measurement and the start of contrast uptake by the vessels. Knowledge of arrival time can be used to calculate blood velocity between the point of contrast injection and the boundary of the region of interest. Furthermore, comparison of arrival times between pre and post treatment curves permits calculation of blood velocity change between the two curves. Label 2 indicates time to peak. Time to peak is the time between the start of contrast uptake and the point of maximum density of contrast in the vessel. The time to peak reflects the flow rate of the contrast. In that regard, shorter times to peak are indicative of greater flow and a healthier vessel. Label 3 indicates wash in rate. Wash in rate is determined based on the slope of the curve. Healthier vessels exhibit greater wash in rates, i.e., steeper slopes. Label 4 indicates width. The width of the curve represents the average time it takes contrast to pass through the vessel. Larger widths suggest longer passage times and unhealthier vessels. Label 5 indicates area under the curve. The area under the curve can be used to estimate the volume of blood flow. Greater blood volume is indicative of a healthier vessel. Label 6 indicates mean transit time. Mean transit time is similar to the width parameter but takes asymmetry of the curve into account.

The parameters may be determined by the image analysis module 112 as described herein, e.g., by analyzing a graphical representation of perfusion imaging data. A physician and/or the medical processing system 102 may use one or more of the parameters to assess a subject's circulation. When the assessment is made before treatment, the assessment can be used to determine the advisability of performing an intravascular procedure. In that regard, the image analysis module 112 may generate a recommendation whether or not to undertake an intravascular procedure, which intravascular procedure to perform, one or more sites at which to perform the intravascular procedure, or combinations thereof. The recommendation may be communicated to the image builder 110 for output to the display 104. When the assessment is made after treatment, the assessment can be used to assess the success of the treatment. In that regard, the image analysis module 112 may generate a recommendation whether or not an additional procedure is advisable, which additional procedure to perform, one or more sites at which to perform the additional procedure, or combinations thereof. The recommendation may be communicated to the image builder 110 for output to the display 104.

In some cases, the parameters may be weighted such that parameters of different weights have different impacts on the assessment of the subject's circulation. For example, a change in a parameter of a higher weight may have a greater impact on the assessment of the subject's circulation than a similar change in a parameter of a lower weight. Each parameter may be assigned a unique weight different from all other parameters. Alternatively, two, three, four, or five parameters may share a certain weight while the remaining one or more parameters have unique weights, share a different weight, or some combination thereof. In that regard, the parameters may be divided into two or more tiers in which parameters within the same tier are assigned the same weight. In an embodiment, arrival time, time to peak, and width may be assigned higher weights than wash in rate, area under curve, and mean transit time. Alternatively, wash in rate, area under curve, and mean transit time may be assigned higher weights than arrival time, time to peak, and width. In an embodiment, width and mean transit time may be assigned the same weight. In an embodiment, one or more of arrival time, time to peak, wash in rate, width, area under the curve, or mean transit time may be assigned the highest weight. In an embodiment, one or more of arrival time, time to peak, wash in rate, width, area under the curve, or mean transit time may be assigned the lowest weight. In an embodiment at least two of weighted parameters may be used to form a composite parameter. In a further embodiment all six parameters are used to for a weighted composite parameter.

Figure 5:
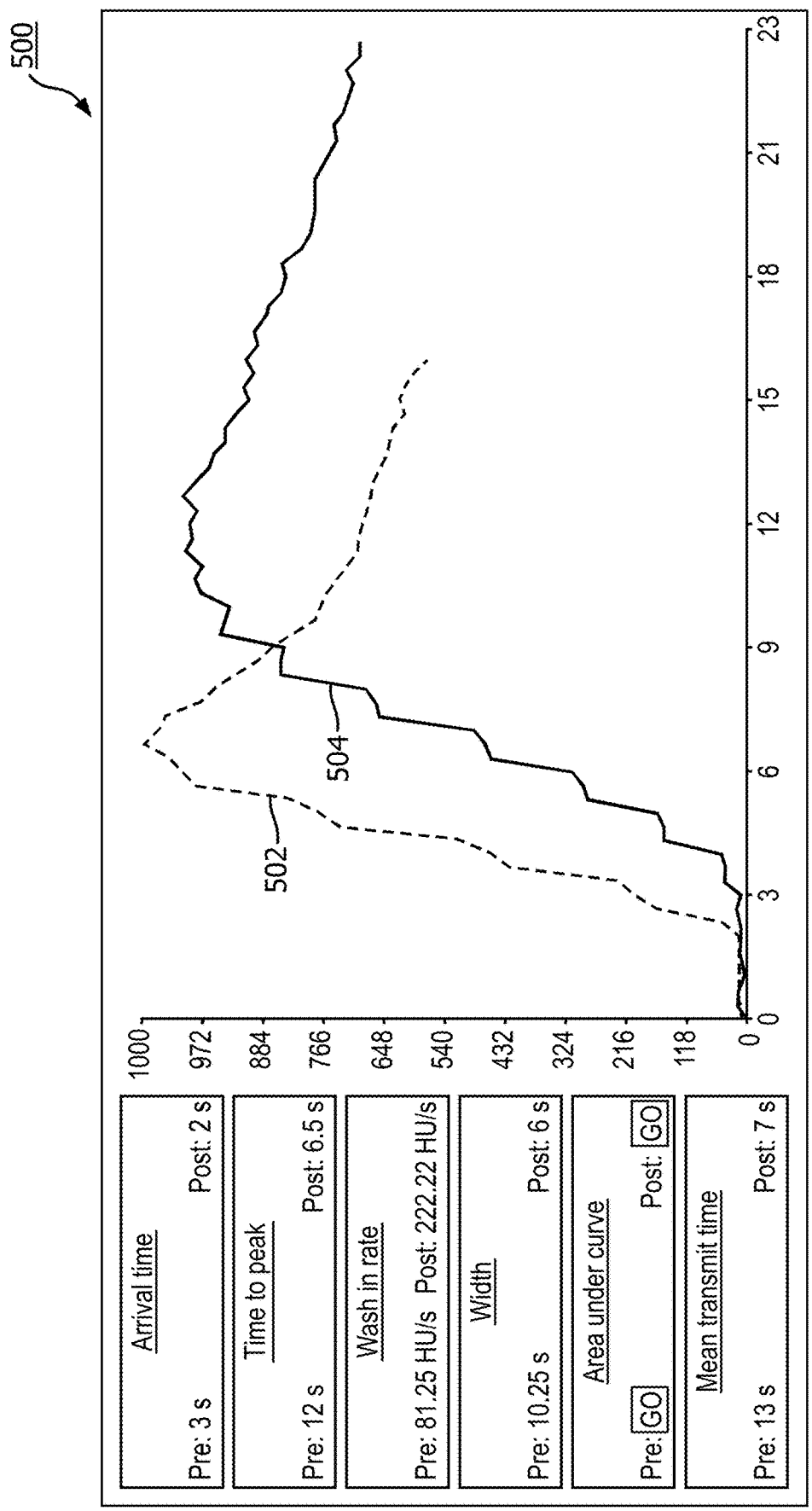
FIG. 5 is a visual display according to another embodiment of the present disclosure.

Turning now to FIG. 5, shown therein is a visual display of an image 500. The image 500 may comprise a graphical user interface in some instances. The image 500 may have been generated by the image builder 110 as described herein and may be displayed on the display 104. The image 500 comprises a graphical representation of two sets of perfusion imaging data, one set obtained prior to performance of an intravascular procedure and the other set obtained after performance of the intravascular procedure. The graphical representation may have been generated based on pre and post-treatment perfusion imaging data for a region of interest, e.g., region of interest 202. In that regard, the image 500 may be displayed along with one or both of the images 200 and 204 either on the same screen or on different screens. The image 500 comprises curve 504 representative of movement of contrast through a vessel of a subject prior to performance of the intravascular procedure and curve 502 representative of movement of contrast through the vessel of the subject after performance of the intravascular procedure. As shown, curve 504 and curve 502 may be plotted on the same set of axes. In FIG. 5, the 'X' axis is representative of time in seconds and the "Y" axis is representative of density in Hounsfield units (HU).

Image 500 further displays six parameters representative of movement of contrast, blood flow, or both, through a vessel of a subject. The six parameters are arrival time, time to peak, wash in rate, width, area under curve, and mean transit time. Though not shown in FIG. 5, image 500 may comprise one or more of labels 1-6 described with reference to FIG. 4 to illustrate how the parameters are determined. For each of the six parameters, image 500 includes both pre-treatment and post-treatment values for the parameter. In some cases, one or both of pre-treatment and post-treatment values for each of the six parameters may be determined automatically, e.g., by the image analysis module 112. Alternatively, one or both of pre-treatment and post-treatment values may be determined in response to user input. For example, FIG. 5 shows that neither the pre-treatment nor the post-treatment value for area under curve has been calculated. Instead, image 500 depicts a "GO" button in place of the values. Accordingly, the value for area under curve may be calculated in response to the user activating the "GO" button. In some circumstances, calculating one or more parameters in response to user input may improve processing time and increase the efficiency of the medical processing system, e.g., medical processing system 102, tasked with determining the values for the parameters by reducing the number of calculations to be performed concurrently. Alternatively or additionally, the difference between pre- and post-treatment parameters may be derived and represented alongside or instead the values of pre- and post-treatment parameters, accentuating the effect of the treatment on the perfusion. In a further alternative embodiment the composite parameter is represented alongside or instead the values of pre- and post-treatment parameters.

Figure 6:
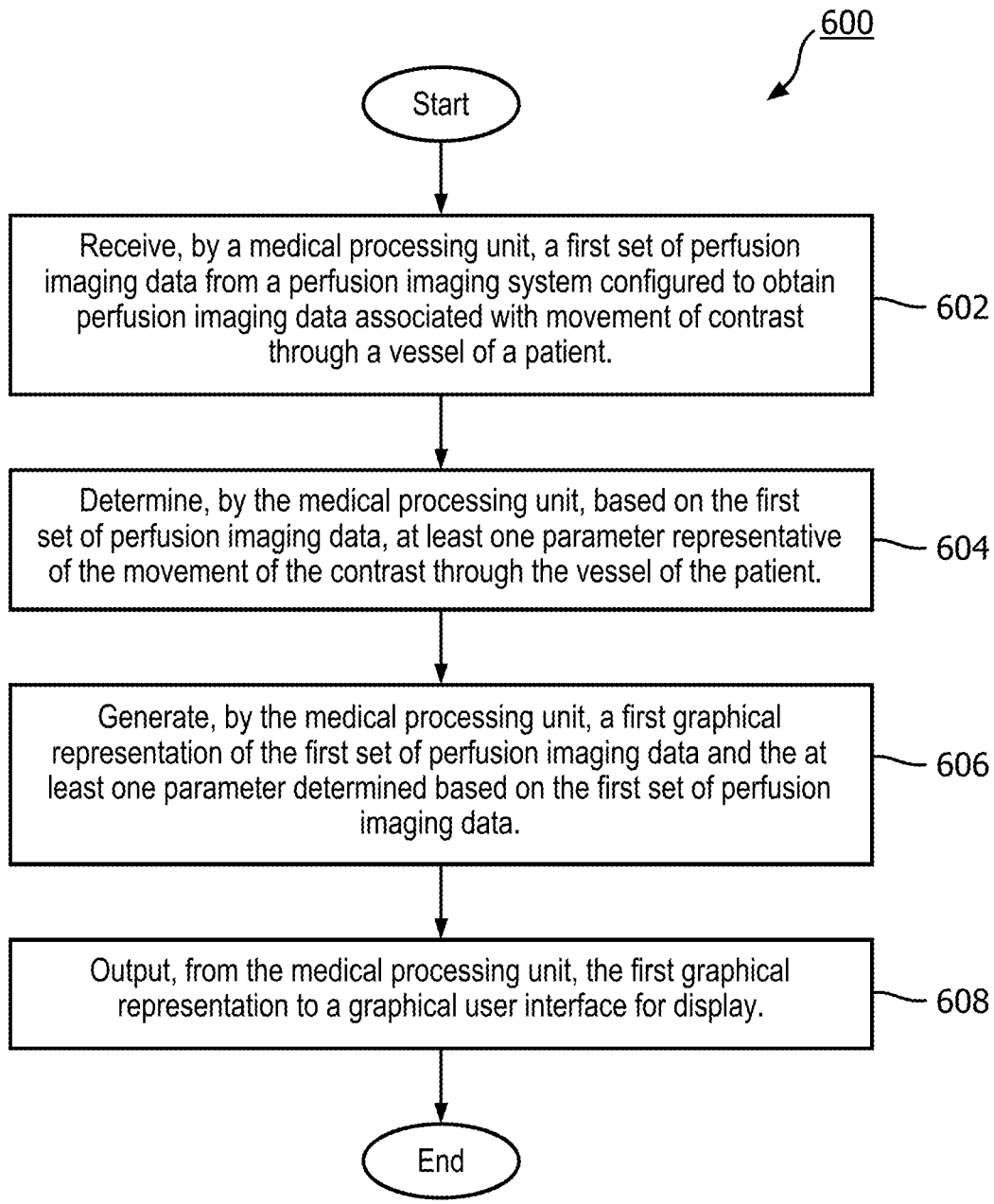
FIG. 6 is a flowchart of a method according to various aspects of the present disclosure.

Referring now to FIG. 6, shown therein is a flow chart of a method 600 according to embodiments of the disclosure. Portions of the method 600 may correspond to techniques discussed hereinabove with reference to FIGS. 1-5 and may be performed on, with, and/or by one or more elements of the system 100. The method begins at block 602 where a first set of perfusion imaging data is received by a medical processing unit from a perfusion imaging system configured to obtain perfusion imaging data associated with movement of contrast through a vessel of a patient. At block 604, determine, by the medical processing unit, based on the first set of perfusion imaging data, at least one parameter representative of the movement of the contrast through the vessel of the patient. Generate, by the medical processing unit at block 606, a first graphical representation of the first set of perfusion imaging data and the at least one parameter determined based on the first set of perfusion imaging data. At block 606, output, from the medical processing unit, the first graphical representation to a graphical user interface for display.

Though not shown in FIG. 6, the method 600 may further comprise additional steps consistent with the foregoing disclosure. For example, the method 600 may comprise generating, by the medical processing unit, a first perfusion image of an anatomical structure based on the first set of perfusion imaging data, and outputting, from the medical processing unit, the first perfusion image to the graphical user interface for display. For further example, the method 600 may comprise generating, by the medical processing unit, a recommendation based on the first set of perfusion imaging data, wherein generating the recommendation comprises identifying one or more candidate sites for an intravascular procedure, and outputting, from the medical processing unit, the recommendation to the graphical user interface for display. For further example, the method 600 may comprise receiving, by the medical processing unit, a second set of perfusion imaging data from the perfusion imaging system, determining, by the medical processing unit, based on the second set of perfusion imaging data, at least one parameter representative of the movement of the contrast through the vessel of the patient, generating, by the medical processing unit, a second graphical representation of the second set of perfusion imaging data and the at least one parameter determined based on the second set of perfusion imaging data, and outputting, from the medical processing unit, the second graphical representation to the graphical user interface for display. For further example, the method 600 may comprise determining, by the medical processing system, the difference between the at least one parameter determined based on the second set of perfusion imaging data and the at least one parameter determined based on the first set of perfusion imaging data, and outputting, from the medical processing system, the difference to the graphical user interface for display. For further example, the method 600 may comprise generating, by the medical processing unit, a second perfusion image of the anatomical structure based on the second set of perfusion imaging data, and outputting, from the medical processing unit, the second perfusion image to the graphical user interface for display.

Further, the method 600 may omit some of the steps shown in FIG. 6 and/or perform the steps in various orders without departing from the scope of the present disclosure.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A medical processing unit configured to:
receive a first set of perfusion imaging data corresponding to a first set of perfusion images from a perfusion imaging system configured to obtain perfusion imaging data associated with movement of contrast through a vessel of a patient;
determine, based on the first set of perfusion imaging data, a first group of at least two parameters representative of the movement of the contrast through the vessel of the patient, wherein the first group of at least two parameters comprises at least two of time to peak, wash in rate, area under curve, or mean transit time;
receive a different, second set of perfusion imaging data corresponding to a different, second set of perfusion images from the perfusion imaging system;
determine, based on the second set of perfusion imaging data, a second group of at least two parameters representative of the movement of the contrast through the vessel of the patient, wherein the second group of at least two parameters is the same as the first group of at least two parameters;
generate a single graphical representation for simultaneous display of the first set of perfusion imaging data, the first group of at least two parameters, the second set of perfusion imaging data, and the second group of at least two parameters; and
output the single graphical representation to a graphical user interface for display,
wherein the first set of perfusion imaging data comprises perfusion imaging data obtained prior to an intravascular procedure and the second set of perfusion imaging data comprises perfusion imaging data obtained after the intravascular procedure, and
wherein the single graphical representation comprises a combination of a first graphical representation for the first set of perfusion imaging data and the first group of at least two parameters and a second graphical representation for the second set of perfusion imaging data and the second group of at least two parameters.

2. The medical processing unit of claim 1, wherein the single graphical representation comprises a first curve representative of the movement of the contrast through the vessel of the patient as shown in the first graphical representation and a second curve representative of the movement of the contrast through the vessel of the patient as shown in the second graphical representation, both plotted on the same set of axes.

3. The medical processing unit of claim 1, further configured to generate a recommendation based on the first group of at least two parameters and to output the recommendation to the graphical user interface for display.

4. The medical processing unit of claim 3, wherein the recommendation comprises identifying one or more candidate sites for the intravascular procedure.

5. A medical system, comprising:
the medical processing unit according to claim 1;
the graphical user interface; and
the perfusion imaging system.

6. The medical system of claim 5, wherein the single graphical representation comprises:
a graph representative of the movement of the contrast through the vessel of the patient, wherein the graph comprises:
a first curve corresponding to the first set of perfusion imaging data; and
a different, second curve corresponding to the second set of perfusion imaging data;
a numerical representation of the first group of at least two parameters; and
a numerical representation of the second group of at least two parameters.

7. A method, comprising:
receiving, by a medical processing unit, a first set of perfusion imaging data corresponding to a first set of perfusion images from a perfusion imaging system configured to obtain perfusion imaging data associated with movement of contrast through a vessel of a patient;
determining, by the medical processing unit, based on the first set of perfusion imaging data, a first group of at least two parameters representative of the movement of the contrast through the vessel of the patient, wherein the first group of at least two parameters comprises at least two of time to peak, wash in rate, area under curve, or mean transit time;
receiving, by the medical processing unit, a different, second set of perfusion imaging data corresponding to a different, second set of perfusion images from the perfusion imaging system;
determining, by the medical processing unit, based on the second set of perfusion imaging data, a second group of at least two parameters representative of the movement of the contrast through the vessel of the patient, wherein the second group of at least two parameters is the same as the first group of at least two parameters;
generating, by the medical processing unit, a single graphical representation for simultaneous display of the first set of perfusion imaging data, the first group of at least two parameters, the second set of perfusion imaging data, and the second group of at least two parameters; and
outputting, from the medical processing unit, the single graphical representation to a graphical user interface for display,
wherein the first set of perfusion imaging data comprises perfusion imaging data obtained prior to an intravascular procedure and the second set of perfusion imaging data comprises perfusion imaging data obtained after the intravascular procedure,
wherein generating the single graphical representation comprises combining a first graphical representation of the first set of perfusion imaging data and the first group of at least two parameters and a second graphical representation of the second set of perfusion imaging data and the second group of at least two parameters.

8. The method of claim 7, further comprising:
determining, by the medical processing unit, the difference between the first group of at least two parameters and the second group of at least two parameters; and
outputting, from the medical processing unit, the difference to the graphical user interface for display.

9. The method of claim 7, wherein the single graphical representation comprises a first curve representative of the movement of the contrast through the vessel of the patient as shown in the first graphical representation and a second curve representative of the movement of the contrast through the vessel of the patient as shown in the second graphical representation both plotted on the same set of axes.

10. The medical processing unit of claim 1, wherein the medical processing unit is further configured to receive a user selection of a region of interest.

11. The method of claim 7, wherein the single graphical representation comprises:
a graph representative of the movement of the contrast through the vessel of the patient, wherein the graph comprises:
a first curve corresponding to the first set of perfusion imaging data; and
a different, second curve corresponding to the second set of perfusion imaging data;
a numerical representation of the first group of at least two parameters; and
a numerical representation of the second group of at least two parameters.

12. The method of claim 7, further comprising:
generating, by the medical processing unit, a first perfusion image of an anatomical structure based on the first set of perfusion imaging data; and
outputting, from the medical processing unit, the first perfusion image to the graphical user interface for display.

13. The method of claim 12, further comprising:
generating, by the medical processing unit, a second perfusion image of the anatomical structure based on the second set of perfusion imaging data; and
outputting, from the medical processing unit, the second perfusion image to the graphical user interface for display.

14. The method of claim 12, further comprising:
generating, by the medical processing unit, a recommendation based on the first set of perfusion imaging data, wherein generating the recommendation comprises identifying one or more candidate sites for the intravascular procedure; and
outputting, from the medical processing unit, the recommendation to the graphical user interface for display.

15. The method of claim 14, wherein identifying one or more candidate sites for the intravascular procedure comprises providing a visual indicator of the one or more candidate sites on the anatomical structure shown in the first perfusion image.

16. The medical processing unit of claim 1, wherein the medical processing unit is further configured to:
determine, only responsive to receiving a user input, an additional parameter representative of the movement of the contrast through the vessel of the patient different than the first group of at least two parameters;
update, based on the additional parameter, the single graphical representation for simultaneous display of the first set of perfusion imaging data, the first group of at least two parameters, the second set of perfusion imaging data, the second group of at least two parameters, and the additional parameter; and
output the single graphical representation to the graphical user interface for display.

17. The medical processing unit of claim 1, wherein the medical processing unit is further configured to:
generate a perfusion image based on a difference between an image of the first set of perfusion images and an image of the second set of perfusion images; and
output the perfusion image to the graphical user interface for display.

* * * * *